United States Patent

Northemann et al.

Patent Number: 5,132,444
Date of Patent: Jul. 21, 1992

[54] GAS-PHASE PREPARATION OF VINYL PHOSPHONIC ACID DERIVATIVES

[75] Inventors: Andreas Northemann; Martin Fischer, both of Ludwigshafen; Ludwig Wambach, Heidelberg, all of Fed. Rep. of Germany

[73] Assignee: BASF Aktiengesellschaft, Ludwigshafen, Fed. Rep. of Germany

[21] Appl. No.: 689,305

[22] Filed: Apr. 22, 1991

[30] Foreign Application Priority Data

May 7, 1990 [DE] Fed. Rep. of Germany ....... 4014483

[51] Int. Cl.$^5$ .................. C07F 9/6574; C07F 9/40; C07F 9/38
[52] U.S. Cl. .................. 558/83; 558/142; 558/215; 558/217; 562/8; 562/25
[58] Field of Search .............. 558/142, 83, 215, 217; 562/8

[56] References Cited

U.S. PATENT DOCUMENTS

| | | | |
|---|---|---|---|
| 3,064,030 | 11/1962 | Chadwick et al. | 548/142 |
| 3,576,924 | 4/1971 | Stamm | 558/152 |
| 3,725,300 | 4/1973 | Stamm | 502/25 |
| 4,386,036 | 5/1989 | Kleiner | 558/142 X |
| 4,388,212 | 6/1983 | Dursch et al. | 558/142 |
| 4,493,803 | 1/1985 | Kleiner et al. | 558/142 |
| 4,894,470 | 1/1990 | Roscher et al. | 558/142 |

OTHER PUBLICATIONS

March, J. Advanced Organic Chemistry; Third Edition; John Wiley and Sons; New York, 1985; pp. 901–905, pp. 914–916.
J. Am. Chem. Soc. 79, 1961 (1957).

Primary Examiner—Mary C. Lee
Assistant Examiner—Michael G. Ambrose
Attorney, Agent, or Firm—John H. Shurtleff

[57] ABSTRACT

A process for the preparation of vinyl phosphonic derivatives of the general formula I

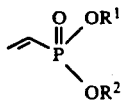

in which $R^1$ and $R^2$ are the same or different and may stand for hydrogen or a $C_1$–$C_8$-alkyl, a $C_6$–$C_{10}$-aryl, or a $C_8$–$C_{10}$-aralkyl radical optionally substituted by Cl or Br, and in which $R^1$ and $R^2$ may alternatively be joined together to form an alicyclic ring having from 3 to 12 carbon atoms in the ring, wherein an ethane phosphonic ester of the general formula II

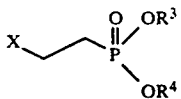

in which $R^3$ and $R^4$ have the meanings stated above for $R^1$ and $R^2$ except for hydrogen and X denotes a hydroxy group, a halogen atom, or a radical of the formula $$-OR^5,$$

in which $R^5$ is a hydrogen atom or a radical of the formula

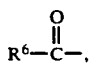

in which $R^6$ is a $C_1$–$C_6$-alkyl radical or an alicyclic ring, is converted in the gas phase in the presence of a solid catalyst.

15 Claims, No Drawings

GAS-PHASE PREPARATION OF VINYL PHOSPHONIC ACID DERIVATIVES

The invention relates to a novel process for the preparation of vinyl phosphonic derivatives of the formula I

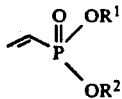

in which $R^1$ and $R^2$ are the same or different and may stand for hydrogen or a $C_1$-$C_8$-alkyl, a $C_6$-$C_{10}$-aryl, or a $C_6$-$C_{10}$-aralkyl radical optionally substituted by Cl or Br, and in which $R^1$ and $R^2$ may alternatively be joined together to form an alicyclic ring having from 3 to 12 carbon atoms in the ring.

The preparation of vinyl phosphonic derivatives in the liquid phase by heating alkyl 2-acetoxy-ethane phosphonates in the presence of acidic or basic catalysts is disclosed in DE-A 3,001,894. However, the yields are unsatisfactory. DE-A 3,120,437 describes a process in which, as in the aforementioned process, a multi-component mixture is formed, and this is reacted with ortho esters to form dialkyl vinyl phosphonates. This two-stage process is complicated and, on account of the high price of the ortho esters, of low economical value. DE-A 3,707,149 describes a method of preparing vinyl phosphonates in which dialkyl vinyl phosphonates are formed in homogenous liquid phase by eliminating acetic acid from dialkyl 2-acetoxy-ethane phosphonates. This method is unsatisfactory from an engineering viewpoint because the reaction products must always be distilled off in vacuo and the space-time yields are poor and the accumulating catalyst residues must be regenerated from time to time.

It is thus an object of the invention to provide measures for overcoming the above drawbacks.

Accordingly, we have found a process for the preparation of vinyl phosphonic derivatives of the formula I

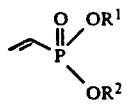

in which $R^1$ and $R^2$ are the same or different and may stand for hydrogen or a $C_1$-$C_8$-alkyl, a $C_6$-$C_{10}$-aryl, or a $C_6$-$C_{10}$-aralkyl radical optionally substituted by Cl or Br, and in which $R^1$ and $R^2$ may alternatively be joined together to form an alicyclic ring having from 3 to 12 carbon atoms in the ring, wherein an ethane phosphonic ester of the formula II

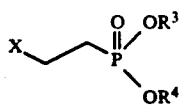

in which X, $R^3$ and $R^4$ have the meanings stated in claim 1, is converted in the gas phase in the presence of a solid catalyst.

The starting compounds II are known from the literature and may be obtained, for example, by reacting diethyl phosphonite or dimethyl phosphonite with a vinyl compound in the presence of a peroxide (J. Amer. Chem. Soc., 79, 1957, pp. 1961–1963).

Suitable starting compounds are ethane phosphonic derivatives of the general formula II, in which X denotes a hydroxy group, a halogen atom such as bromine and, in particular, chlorine, or especially a radical of the formula

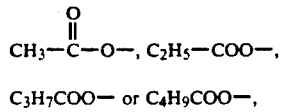

$C_3H_7COO-$ or $C_4H_9COO-$, $R^3$ and $R^4$ may denote identical or different radicals preferably selected from the following:

alkyl, such as $C_1$-$C_8$-alkyl, preferably $C_1$-$C_4$-alkyl such as methyl, ethyl, n-propyl, isopropyl, n-butyl, isobutyl, and s-butyl, particularly methyl and ethyl;

aryl or aralkyl, such as phenyl and, in particular, benzyl.

$R^3$ and $R^4$ can be interconnected to form an alicyclic ring having from 3 to 12 carbon atoms in the ring.

We particularly prefer to convert compounds of the general formula II in which $R^3$ and $R^4$ are the same or different and denote methyl or ethyl.

Suitable catalysts are principally phosphates, acid oxides, particularly those of silicon, aluminum, and boron, and supporting materials containing acidic substances. Such acidic substances are suitably mineral acids or their acid salts, such as sodium dihydrogen phosphate or sodium bisulfate. Particularly preferred catalysts are silica gels, for example silica gel $D_{11\text{-}10}$® or aluminum oxide, for example, aluminum oxide $D_{10\text{-}20}$®.

Other preferred catalysts are supporting materials doped with from 0.1 to 20% w/w and in particular with from 1 to 5% w/w of alkali metal or alkaline earth metal oxides, the preferred supports being aluminum oxide or silica gel in neutral form.

The following are preferred catalysts:

Catalyst A:
Commercial $SiO_2$ ($D_{11\text{-}10}$®, BASF) in the form of rods.

Catalyst B:
Commercial $Al_2O_3$ ($D_{10\text{-}20}$®, BASF) in the form of rods.

Catalyst C:
Catalyst A impregnated with phosphoric acid, dried at 110° C. and calcined at 500° C. for 14 hours. It contains 28.97% w/w of $P_2O_5$.

Catalyst D:
Catalyst A impregnated with boric acid, dried at 110° C. and calcined at 500° C. for 14 hours. It contains 10.2% w/w of $B_2O_3$.

Catalyst E:
Catalyst B impregnated with caustic soda solution, dried at 110° C. and calcined at 500° C. for 14 hours. It contains 1.5% w/w of $Na_2O$.

The ratio of educt to catalyst is preferably from 0.01 to 10 g and more preferably from 0.1 to 3 g of educt per g of catalyst per hour under continuous-flow conditions.

The reaction is usually carried out in a reaction tube which is filled with the catalyst and heated.

The reaction is preferably carried out at a temperature of from 250° to 400° C. and more preferably from 260° to 300° C. Though possible, the use of temperatures above or below this range does not generally provide any improvement.

The process may be carried out batchwise or, preferably, continuously, in which case it is recommended that the reactants be caused to sojourn in the catalyst zone for from 0.05 to 60 seconds and preferably from 0.5 to 10 seconds in order to achieve high selectivity.

For the purposes of controlling the sojourn time and diluting the reactants, the gas mixture is preferably mixed with inert carrier gases.

To this end, the starting compounds are usually evaporated in an upstream evaporator at a temperature of from 180° to 270° C. and preferably from 200° to 250° C., during which operation they are mixed with the carrier gases.

Suitable carrier gases are the conventionally employed gases which are inert under the reaction conditions, such as nitrogen, hydrogen, steam, carbon dioxide, and argon, and preferably low-boiling alcohols such as methanol and ethanol. Alcohol/inert gas mixtures are particularly preferred. The use of an alcohol increases the useful life of the catalyst. The alcohol is added to the starting product in a molar ratio of from 10:1 to 0.1:1 and in particular from 0.5:1 to 5:1.

The process may be carried out under reduced to elevated pressures ranging, for example, from 10 mbar to 5 bar; but preferably atmospheric pressure conditions are used.

No special methods are employed for working up the product, which may be directly treated to yield the vinyl phosphonic acid or subjected to distillation to obtain the vinyl phosphonate.

The process of the invention is particularly significant with regard to the synthesis of vinyl phosphonic derivatives of the general formula I in which $R^1$ and $R^2$ are the same or different and denote hydrogen, methyl, or ethyl, by eliminating acetic acid from dimethyl 2-acetoxyethanephosphonate.

Vinyl phosphonic derivatives are intermediates in the synthesis of vinyl phosphonic acid and also constitute monomers for the preparation of adhesives and synthetic resins.

EXAMPLES 1 to 6

A mixture of dialkyl acetoxyethanephosphonate and alcohol in molar ratio y was evaporated at 220° C. and passed over the catalyst at a temperature of 270° C. together with nitrogen flowing at a rate of 40.0 l/h such that the sojourn time in the catalyst zone was 3.5 seconds. The reaction product was condensed. Further experimental details are listed in Table 1 below. Catalysts A to D are those described above.

EXAMPLE 7

Bis-chloroethyl chloroethanephosphonate (0.05 mole/h) was evaporated at 220° C. and passed over catalyst E at 270° C. together with nitrogen flowing at a rate of 50.5 l/h. The material discharged after an on-stream period of 3 hours consisted of 85% starting material and 15% bis-chloroethyl vinyl phosphonate.

We claim:

1. A process for the preparation of a vinyl phosphonic derivative of the formula

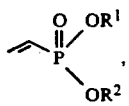   I in which $R^1$ and $R^2$ are the same or different and each represents hydrogen or a hydrocarbon substituent selected from the group consisting of $C_1$–$C_8$-alkyl, $C_6$–$C_{10}$-aryl, and $C_6$–$C_{10}$-aralkyl optionally substituted by Cl or Br, and in which $R^1$ and $R^2$ may also be joined together as an alkylene chain to form an alicyclic ring having from 3 to 12 carbon atoms in the ring, which process comprises:

converting an ethane phosphonic ester of the formula

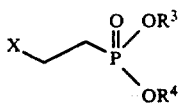   II in which $R^3$ and $R^4$ have the meanings stated above for $R^1$ and $R^2$ except for hydrogen and X denotes a halogen atom, or a radical of the formula

—$OR^5$, in which $R^5$ is a hydrogen atom or a radical of the formula

in which $R^6$ is $C_1$–$C_6$-alkyl, in the gas phase and in the presence of a solid catalyst selected from the group consisting of phosphates, an acid oxide, and an acid oxide supporting material impregnated with an acidic substance, an alkali metal oxide, or an alkaline earth metal oxide.

TABLE 1

| Ex. | $R^1$ | $R^2$ | X | y | Duration of test (h) | Catalyst | Compounds (%) 1 | 2 | 3 |
|---|---|---|---|---|---|---|---|---|---|
| 1 | methyl | methyl | acetoxy | 1:1 | 6 | A | 49 | 28 | 9 |
| 2 | methyl | methyl | acetoxy | 1:1 | 6 | B | 40* | | |
| 3 | methyl | methyl | acetoxy | 1:1 | 6 | C | 52 | 23 | 4 |
| 4 | methyl | methyl | acetoxy | 1:1 | 6 | D | 46 | 24 | 12 |
| 5 | ethyl | ethyl | acetoxy | 1:1 | 6 | A | 41 | 15 | 3 |
| 6 | ethyl | ethyl | acetoxy | 1:1 | 6 | C | 45 | 14 | 7 |

Compound 1: $R^1$ as in starting compound $R^2$ as in starting compound
Compound 2: $R^1$ as in starting compound $R^2$ hydrogen
Compound 3: $R^1$ hydrogen $R^2$ hydrogen
*remainder = educt 2. A process as claimed in claim 1, wherein the catalyst used is a phosphate, acid oxide, or an acid oxide support containing an acidc substance.

3. A process as claimed in claim 1, wherein the catalyst used is an acid oxide of an element selected from the group consisting of Si, B and Al.

4. A process as claimed in claim 1, wherein the catalyst used is an acid oxide support containing from 0.1 to 20% w/w of alkali metal or alkaline earth metal oxide.

5. A process as claimed in claim 1, wherein the conversion is carried out in the gas phase at a temperature of from 250° to 400° C.

6. A process as claimed in claim 1, wherein the conversion reaction is carried out continuously over said solid catalyst, and the sojourn time of the ester reactant II over the catalyst is from 0.05 to 60 seconds.

7. A process as claimed in claim 1, wherein the ester reactant II is diluted with a carrier gas which is inert under the reaction conditions.

8. A process as claimed in claim 7, wherein the carrier gas used is selected from the group consisting of methanol, ethanol, nitrogen, hydrogen, carbon dioxide, argon, steam and mixtures thereof.

9. A process as claimed in claim 1, wherein the catalyst used is $SiO_2$.

10. A process as claimed in claim 1, wherein the catalyst used is $Al_2O_3$.

11. A process as claimed in claim 1, wherein the catalyst used is $SiO_2$ impregnated with phosphoric acid.

12. A process as claimed in claim 1, wherein the catalyst used is $SiO_2$ impregnated with boric acid.

13. A process as claimed in claim 1, wherein the catalyst used is silica gel or aluminum oxide doped with an alkali metal or alkaline earth metal oxide.

14. A process as claimed in claim 1, wherein the conversion is carried out in the gas phase at a temperature of from 260° to 300° C.

15. A process as claimed in claim 1, wherein the conversion is carried out to prepare a vinyl phosphonic derivative of the formula I in which $R^1$ and $R^2$ are the same or different and denote hydrogen, methyl or ethyl, by eliminating acetic acid from dimethyl 2-acetoxyethanephosphonate.

* * * * *